United States Patent
Lee et al.

(10) Patent No.: US 8,979,908 B2
(45) Date of Patent: *Mar. 17, 2015

(54) TRANSVERSE FIXATION DEVICE FOR SPINAL FIXATION SYSTEMS

(71) Applicant: Globus Medical, Inc., Audubon, PA (US)

(72) Inventors: Andrew Lee, Santa Rose, CA (US); Andrew Iott, Villanova, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/084,175

(22) Filed: Nov. 19, 2013

(65) Prior Publication Data

US 2014/0074172 A1 Mar. 13, 2014

Related U.S. Application Data

(63) Continuation of application No. 13/228,663, filed on Sep. 9, 2011, now Pat. No. 8,613,759, which is a continuation of application No. 10/885,841, filed on Jul. 8, 2004, now Pat. No. 8,034,082.

(51) Int. Cl.
*A61B 17/88* (2006.01)
*A61B 17/70* (2006.01)

(52) U.S. Cl.
CPC ................... *A61B 17/7052* (2013.01)
USPC ........... 606/279; 606/250; 606/276; 606/277; 606/278

(58) Field of Classification Search
CPC .. A61B 17/88; A61B 17/7049; A61B 17/705; A61B 17/7052; A61B 17/7043
USPC .................. 606/250–253, 259–260, 276–279
See application file for complete search history.

(56) References Cited

U.S. PATENT DOCUMENTS

| | | | |
|---|---|---|---|
| 5,010,879 A | 4/1991 | Moriya et al. |
| 5,380,325 A | 1/1995 | Lahille |
| 5,676,665 A | 10/1997 | Bryan |
| 6,090,111 A | 7/2000 | Nichols |
| 6,565,565 B1 | 5/2003 | Yuan et al. |
| 6,669,729 B2 | 12/2003 | Chin |
| 6,740,086 B2 | 5/2004 | Richelsoph |
| 6,755,829 B1 | 6/2004 | Bono et al. |
| 6,786,903 B2 | 9/2004 | Lin |
| 7,081,117 B2 | 7/2006 | Bono et al. |
| 7,125,426 B2 | 10/2006 | Moumene et al. |
| 7,261,714 B2 | 8/2007 | Richelsoph |
| 7,282,064 B2 | 10/2007 | Chin |
| 2002/0120272 A1 | 8/2002 | Yuan et al. |
| 2005/0080416 A1 | 4/2005 | Ryan et al. |
| 2005/0119657 A1 | 6/2005 | Goldsmith |
| 2005/0228326 A1 | 10/2005 | Kalfas et al. |
| 2006/0200128 A1 | 9/2006 | Mueller |
| 2007/0299446 A1 | 12/2007 | Chin |
| 2008/0045955 A1 | 2/2008 | Berrevoets et al. |

*Primary Examiner* — Eduardo C Robert
*Assistant Examiner* — Julianna N Harvey

(57) ABSTRACT

A transverse fixation device is disclosed. The device includes one or more connecting bodies disposed substantially between two elongate rods. Each connecting body includes a receptacle that is capable of engaging with the two elongate rods. A c-ring comprising an outer surface having a spherical curvature is also included. A third rod may be inserted into the c-ring. A clamp included in the connecting bodies may then be disposed about the c-ring and third rod to allow the connecting bodies to slidingly engage with the third rod.

20 Claims, 3 Drawing Sheets

TRANSVERSE FIXATION DEVICE FOR SPINAL FIXATION SYSTEMS

CROSS REFERENCE TO RELATED APPLICATIONS

This patent application is a continuation application claiming priority to U.S. patent application Ser. No. 13/228,663 filed on Sep. 9, 2011 which is a continuation application claiming priority to U.S. patent application Ser. No. 10/885,841, filed on Jul. 8, 2004, the entire contents of which are incorporated by reference.

FIELD OF THE INVENTION

The present invention relates to spinal fixation systems. More specifically, the present invention relates to a transverse fixation device capable of ensuring a connection between two rods of a spinal fixation system.

BACKGROUND OF THE INVENTION

The human spine is particularly important because it protects the spinal cord, which is responsible for relaying electrical impulses from the brain to the rest of the body. Occasionally, an accident or other outside force may cause the vertebrae which make up the spine to be broken, cracked, or chipped. Each of these situations are dangerous, and are handled by the most skilled physicians and surgeons. The remedy for a broken, cracked, or chipped bone may be different for every individual, and may change according to the situation under which the injury occurred.

One situation that commonly arises occurs is when vertebrae or portions of vertebrae or spine are broken, cracked, or are beginning to fail to function normally. One treatment technique used by doctors to remedy this situation involves using a pair of rods that are connected to several vertebrae. The rods may be aligned along the periphery of the vertebrae, and are typically used to maintain the alignment of the bones. This may allow the vertebrae to re-grow bony tissue or cartilage. In addition, aligning the vertebrae allows them to heal properly, and prevents movement of the spine from injuring the spinal cord.

In order to prevent the movement of the spine, a fixation system is often used to hold the two rods together. The fixation system allows the rods to be fixed in place under normal conditions. Many fixation devices are currently available. They vary in shape, size, and their approach to preventing the rods from moving. One type of device that has been used involves a single connection body that lies in between the two rods, over the body of the vertebrae. Though this device serves the purpose of preventing the rods from moving, it also has several disadvantages. For example, many of these devices are unable to move, rendering them unable to adapt to the contour of the spine. Another limitation of these devices is that they typically do not allow for clearance of the body of the vertebrae, which can cause damage to the vertebrae or cause the device to protrude from underneath a person's skin.

Many devices hold the rods in place by gripping them from the outer portion of the bars. These devices also achieve the purpose of holding the bars in place, but have several limitations. For instance, these devices often man not be capable of achieving the same degree of grip on the rods as compared to a configuration that grips the bars from the inner area, between the bars.

Other devices have aimed to eliminate the limitations of their predecessors by providing two connecting bodies that have a small degree of adjustability. However, many of these devices are unable to translate axially, which prevents them from adjusting to the spacing between the rods. Other devices are unable to rotate to adjust for rods that aren't coplanar. Additionally, these devices often do not have the ability to rotate freely, preventing them from adjusting to the contours of the spine. Devices such as these may provide greater adjustability at the expense of increased complexity, number of components, increased overall height, or other limitations and disadvantages.

A continuing need exists for a spinal fixation system that is able to adjust the contours of the spine.

SUMMARY OF THE INVENTION

The present invention comprises a transverse fixation device. The device preferably comprises a first and second elongate rod and a c-ring. The c-ring may include an outer surface having a spherical curvature and first and second free ends facing each other to define an opening. Also included may be a third elongate rod and a connecting body. The connecting body may be disposed substantially between the first and second elongate rods and may comprise a receptacle facing outwards towards the first rod and away from the second rod and a set screw selectively positioned to securely hold the connecting body to the first rod. Preferably, a clamp disposed around the c-ring and the third rod having a curved surface corresponding to the outer surface of the c-ring and a set screw capable of securing the clamp to the connecting body are also included.

In one embodiment, the c-ring and clamp allow the connecting body to slidingly engage with the third rod. Preferably, the c-ring comprises an inner surface having a substantially cylindrical shape. It may be desired to have the c-ring comprise a notch selectively positioned substantially opposite the opening. The connecting body may slidingly engage with the third rod to translate axially. In another embodiment, the connecting body is capable of rotating about a transverse axis. In other embodiments, the connecting body is capable of rotating about an axis perpendicular to a transverse axis. In these embodiments, the rotation may be between about 5 and 25 degrees. More preferably, the rotation may be between about 10 and 15 degrees.

In another embodiment, the present invention comprises a transverse fixation device comprising a first and second elongate rod and a c-ring. The c-ring may include an outer surface having a spherical curvature and first and second free ends facing each other to define an opening. Also included may be a third elongate rod and a first and second connecting body. Preferably, the first and second connecting bodies are disposed substantially between the first and second elongate rods and include a receptacle facing outwards towards the first rod and away from the second rod. The second connecting body comprises a receptacle facing outwards towards the second rod and away from the first rod and a first set screw selectively positioned to securely hold the connecting body to the first rod. A second set screw may be selectively positioned to securely hold the connecting body to the second rod. A clamp may be disposed around the c-ring and third rod. Preferably the clamp has a curved surface corresponding to the outer surface of the c-ring and a set screw capable of securing the clamp to the connecting body. In this embodiment, the c-ring and clamp allow the connecting body to slidingly engage with the third rod.

In one embodiment, the third rod is offset from the first and second connecting bodies. In other words, the third rod does not lie in the same plane as the first and second connecting bodies. In prior art fixation systems, a rod's size was limited because it was in the same plane as the connecting bodies and had to slidingly engage with the bodies. However, in the present invention the length of the third rod may be varied as desired because it does not lie in the same plane as the connecting bodies. Rather, the third rod engages with a clamp that is included with the first and second connecting bodies, as described above. One advantage of allowing the length of the third rod to be varied is that the distance between the two connecting bodies does not have to be limited. Another advantage is that rod's with a predetermined length may be mass produced and used with fixation systems in any part of the spine. This may reduce both the cost and complexity of the present invention.

In one embodiment, the connecting body may be capable of rotating about a transverse axis. In this embodiment, the degree of rotation may be about 90 degrees or less. More preferably, the degree of rotation is about 180 degrees or less. In some embodiments, the connecting body may be capable of a degree of rotation about a transverse axis that is about 360 degrees or less. Preferably, the first and second set screws are positioned at between about a 1 and 10 degree angle relative to a horizontal axis. The clamp may be capable of holding the first and second body in place relative to the c-ring and the third rod.

In another embodiment, the present invention comprises a transverse fixation device comprising a first and second elongate rod and a c-ring. Preferably, the c-ring comprises an outer surface having a spherical curvature and first and second free ends facing each other to define an opening. Also included may be a third elongate rod, a connecting body, and a clamp disposed around the c-ring and third rod. Preferably, the clamp has a curved surface corresponding to the outer surface of the c-ring and a set screw capable of securing the clamp to the connecting body. The c-ring and clamp preferably allow the connecting body to slidingly engage with the third rod.

In one embodiment, the connecting body is capable of translating axially relative to the third rod. In another embodiment, the connecting body is capable of rotating about an axis perpendicular to a transverse axis. Preferably, this rotation is between about 10 and 30 degrees. More preferably, the rotation is between about 15 and 20 degrees. In some embodiments, the c-ring comprises a notch positioned substantially opposite the opening. To accommodate a round third rod, the c-ring comprises a cylindrical inner surface.

DETAILED DESCRIPTION OF THE PREFERRED EMBODIMENTS

The human body comprises many bones which together allow the body to have a defined structure. Many bones are responsible for protecting vital organs of the human body. The spine comprises a plurality of vertebrae that are responsible for protecting the spinal cord. The spinal cord allows the brain to communicate with various other parts of the body. Occasionally, the spine is subjected to forces that cause the structural integrity of one or more vertebrae to be compromised. Such forces may cause one or more vertebrae to be, for example, fractured or broken. When the structural integrity of the vertebrae are compromised, the bones may leave the spinal cord vulnerable, which is highly undesirable. Because the spinal cord is so important to allowing a human being to function, doctors must often temporarily or permanently restore the structural integrity of the vertebrae.

Figure 1:
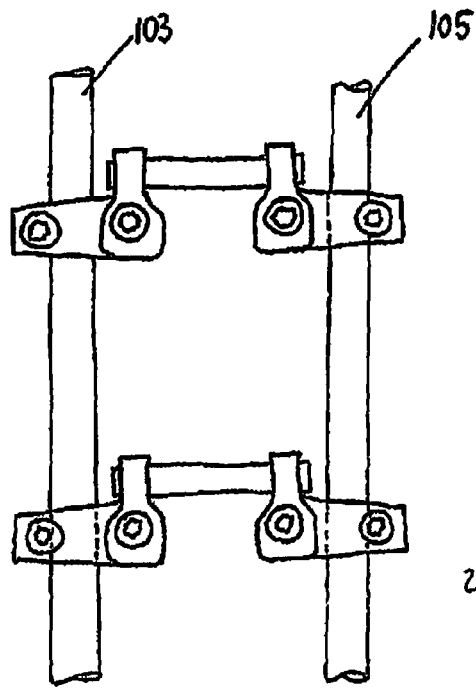
FIG. 1 is a diagram showing rods used in an exemplary spinal fixation system.

Many apparatus have been used to correct the structural integrity of vertebrae. For instance, outside forces may sometimes require vertebrae to be aligned using, for example, at least two rods. As shown in FIG. 1, two rods 103 and 105 preferably run along the length of the two or more vertebrae 101. Each rod 103-105 is preferably fixed to the vertebrae. Many methods for fixing rods to vertebrae are well known to those skilled in the art, and are not the subject of the present invention. In order to align the two or more vertebrae, the rods 103-105 are preferably held in place using, for example, a fixation device. Typically, these devices are referred to as transverse fixation devices. However, prior art fixation devices have several disadvantages. For example, some fixation devices have large profiles, which cause them to protrude under the skin. Other devices are unable to provide adequate clearance for the body of the vertebrae, which may differ between individuals and the region of the spine in which the rods 103-105 are used. Still other devices have rigid, fixed bodies. This prevents the device from adapting to rods 103-105 that are not located within the same plane. Furthermore, a rigid, fixed connecting body prevents a doctor from adapting the fixation device to the amount of separation between the rods 103-105. This can prolong the time required for surgery or require additional surgeries to correct complications that may result.

The present invention is capable of substantially minimizing the disadvantages of prior art fixation devices that are used with spinal fixation devices. Preferably, the present invention comprises two connecting bodies that are capable of passing a rod used in a spinal fixation device. Each of the two connecting bodies are preferably capable of remaining fixed to the two rods 103-105. The two connecting bodies are preferably connecting using a third rod, which allows the two rods 103-105 to be fixed in place relative to one another. As described above, this may be particularly desirable in spinal fixation devices that seek to align two or more vertebrae. Each of the two connecting bodies preferably comprises an opening for passing the third rod that is capable of fixing the connecting body in place relative to the third rod using, for example, a screw. The opening preferably includes a c-ring having a spherical curvature, which may be placed within the opening to pass the third rod. The spherical curvature of the c-ring preferably prevents it from being forced out of the opening under normal conditions. The c-ring may be capable of allowing the two connecting bodies to translate axially, or side to side, with respect to the third rod. This allows the spacing between the two rods 103-105 to be adjusted during, for example, an operation. Additionally, the c-ring preferably allows the two connecting bodies to accommodate two bars 103-105 that are not within the same plane. Thus, the two connecting bodies are capable of being adjusted to accommodate the placement of the two rods 103-105. Once the two connecting bodies are positioned as desired, they may be fixed in place relative to the third rod.

Figure 2A:
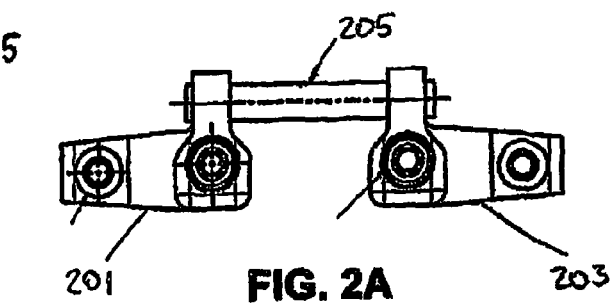
FIGS. 2A-2C are diagrams showing one embodiment of the present invention.
Figure 2B:
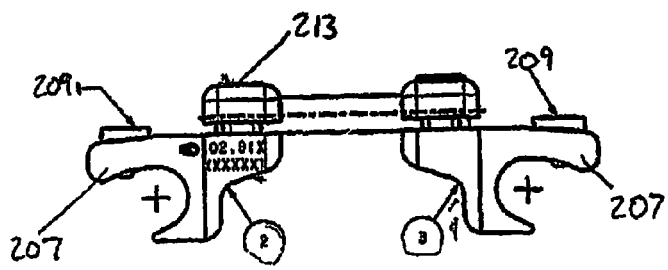
Figure 2C:
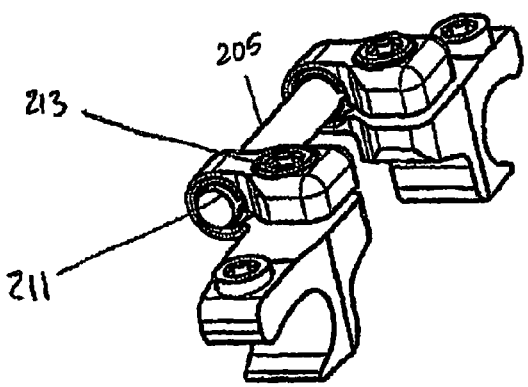

FIGS. 2A-2C are diagrams showing one embodiment of the present invention. In one embodiment, the present invention comprises two connecting bodies 201-203 and a rod 205, as shown in FIG. 2A. Each connecting body 201-203 may be operatively connected to the rod 205 by passing the rod through, for example, an opening in connecting body 201-203. As shown in FIG. 2B, each connecting body 201-203 may have a receptacle 207 that is configured and dimensioned to engage with rods 103-105 from the inside. Preferably, a set screw 209 may be included to prevent the connecting bodies 201-203 from disengaging from the rods 103-105. In one embodiment, each connecting body 201-203 also includes a collar 211, through which the rod 205 may pass. Preferably, the rod 205 passes through a c-ring, which is then inserted into the opening of the collar 211. Passing the rod 205 through the c-ring to allow the connecting bodies 201-203 to be rotated relative to the rod 205. As mentioned above, this allows the present invention to adjust to the relative placement of rods 103-105. The collar 211 may be capable of being flexed such that an object, such as the c-ring may be easily inserted into its opening. Once the c-ring and rod 205 are inserted into the opening, it may be tightened around the c-ring and rod 205 by using, for example, a screw 213.

In one embodiment, the present invention may comprise any material, or combination of materials. The materials may include, but are not limited to, a metal or alloy. In some embodiments, steel, titanium, iron, and the like may be used. The type of material that is used may be chosen such that it has sufficient strength to maintain the rods 103-105 in a substantially fixed manner under normal conditions. Normal conditions, as described, will be understood to be conditions that a healthy spine may be subjected to without causing the structural integrity of the vertebrae to be compromised. This may include, for example, using a material that is capable of maintaining its structural integrity when subjected to the conditions present inside the human body. Thus, it may be desirable to use a material that does not corrode or otherwise cause any harmful side-effects within a body.

Figure 3:
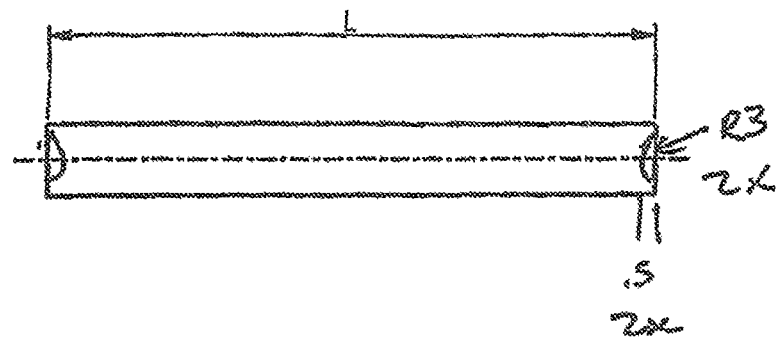
FIG. 3 is a diagram showing one embodiment of a rod shown in FIGS. 2A-2C.

FIG. 3 is a diagram showing one embodiment of a rod shown in FIGS. 2A-2C. Preferably, the rod may have any desired dimensions. For example, in one embodiment the length of the rod may be chosen such that it is at least as long as the width of the widest vertebra. One advantage of this embodiment is that the length of the rod may be sufficient to allow the connecting bodies 203-205 to engage with rods 103-105 while still being able to be fixed to rod 205. In another embodiment, it may be desirable to substantially minimize the length of the rod while still providing sufficient length to allow the connecting bodies 203-205 to engage with the rods 103-105. One advantage of this embodiment is that the profile of the present invention may be reduced while still fixing the rods 103-105 relative to one another. Preferably, the length of the rod 205 may be about 5 cm or less. More preferably the length of the rod may be about 4 cm or less, and most preferably the length of the rod 205 may be about 3 cm or less.

In one embodiment, the rod 205 may be substantially circular. In this embodiment, the radius of the rod 205 may be chosen such that it is able to pass through opening 211. In another embodiment, the radius of the rod 205 may be chosen such that it is able to pass through the c-ring, described with reference to FIGS. 2A-2C. In other embodiments, it may be desirable choose the radius of the rod 205 to be sufficient to prevent deformation under normal conditions imposed within a body. However, it may sometimes be desirable to limit the radius of the rod 205 to substantially minimize the profile of the present invention. Preferably, the radius of the rod 205 may be less than about 1 cm. More preferably, the radius of the rod 205 may be less than about 8 mm, and most preferably the radius of the rod 205 may be less than about 4 mm.

Figures 4A, 4B:
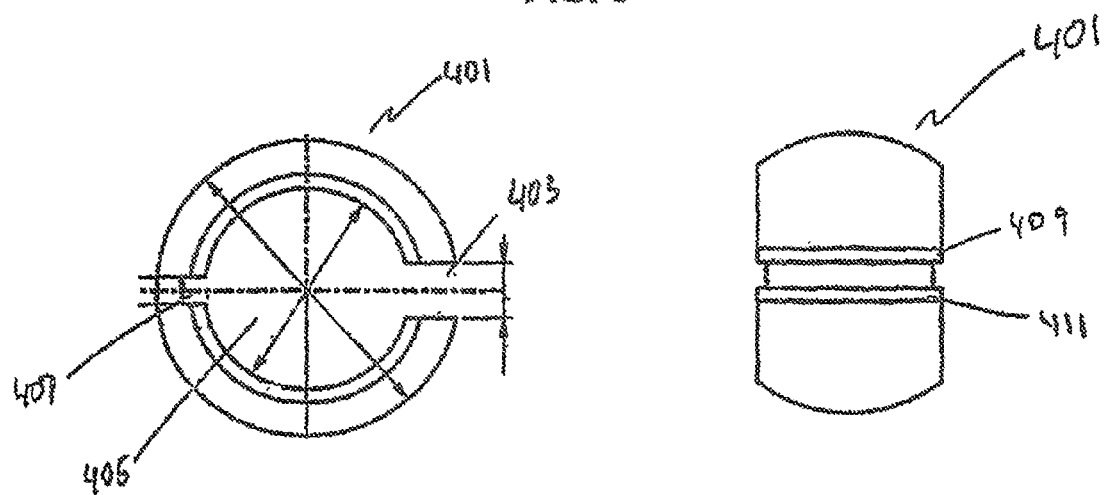
FIGS. 4A-4B are diagrams showing one embodiment of a c-ring.

FIGS. 4A-4B are diagrams showing one embodiment of a c-ring. As mentioned above, the c-ring 401 may be selectively positioned within the opening of the collar 211. In one embodiment, after selectively positioning the c-ring 401 within the opening of the collar 211, the rod 205 may pass through the c-ring 401. In another embodiment, the rod 205 may pass through the c-ring 401 before it is selectively positioned within the opening of the collar 211. Preferably, the c-ring 401 provides a receptacle for the rod, 205 that is configured and dimensioned such that at least a portion of the inner surface of the c-ring is capable of maintaining a sufficient grip on the rod 205. In other words, the inner surface of the c-ring 401 preferably achieves sufficient contact with the outer surface of the rod 205 such that the c-ring 401 may be tightened around the rod 205 to substantially prevent any relative movement between the two.

In one embodiment, the length of the c-ring 401 may be chosen such that it is substantially the same as the length of the opening of the collar 211. In another embodiment, the c-ring 401 may be slightly longer than the length of the opening of the collar 211. In other embodiments, the length may be chosen according to the dimensions of the rod 205. In these embodiments, the length of the c-ring may be substantially larger for rods 205 having greater lengths or diameters. Conversely, the length of the c-ring 401 may be substantially smaller for rods 205 having smaller lengths or diameters. Preferably, the length of the c-ring may be about 30 mm or less. More preferably, the length of the c-ring may be about 20 mm or less, and most preferably the length of the c-ring may be about 10 mm or less.

In one embodiment, as shown in FIG. 4A, the c-ring 401 comprises a discontinuous cylindrical shape. Preferably, the discontinuity 403 allows the c-ring 401 to be flexed according to the size of an object that is inserted into its opening 405. Preferably, width of the discontinuity may be about 10 mm or less. More preferably the width of the discontinuity may be about 6 mm or less, and most preferably the width of the discontinuity may be about 4 mm or less. Another way to describe the discontinuity 403 is as a percentage of the total circumference of the cylindrical c-ring 401. Preferably, the discontinuity may be about 10% or less of the total circumference. More preferably, the discontinuity may be about 5% or less of the total circumference, and most preferably the discontinuity may be about 2.5% or less of the total circumference.

The dimensions of the c-ring 401 may be changed according to a particular application. For example, in one embodiment, the inner surface of the c-ring 401 may be substantially uniform and cylindrical, as shown in FIG. 4B. One advantage of a substantially uniform and cylindrical inner surface may be that the substantially cylindrical outer surface of rod 205 may sit flush with the cylindrical inner surface. Allowing the two surfaces to be flush substantially increases the surface area that is in contact, thereby increasing the amount of friction between the inner surface of the c-ring 401 and the outer surface of the rod 205. This may minimize the chance of movement between the two in embodiments where the c-ring 401 is tightened around the rod 205. In one embodiment, as mentioned above, the c-ring 401 may be tightened around rod 205 such that relative movement between the two is substantially minimized. This may be desirable in embodiments where it may be preferred to hold rods 103-105 (FIG. 1) in place relative to one another. In such an embodiment, it may be desirable to substantially maximize the surface area in contact between the c-ring 401 and the rod 205.

In one embodiment, the outer surface of the c-ring 401 may also be substantially uniform and cylindrical. One advantage of a uniform and cylindrical outer surface is that the connecting bodies may rotate around it within substantially 360 degrees of freedom. As described above, this allows the connecting bodies to adjust to the placement of rods 103-105. In another embodiment, the c-ring 401 may be placed at any two points along the surface of the rod 205, which allows axial translation of the connecting bodies. Once the c-ring 401 is fastened to the rod 205, the connecting bodies may no longer be axially translated.

In one embodiment, the inner surface of the c-ring 401 may include a notch 407. In this embodiment, the notch 407 may be positioned substantially directly opposite the discontinuity 403. One advantage of this positioning may be that the structural integrity of the c-ring 401 may not be as high in the area around the notch 407. Thus, when pressure is applied to one or more points on the outer surface of the c-ring 401, the area substantially around the notch 407 may be more likely to deform. One advantage of this embodiment is that placing the notch 407 substantially directly opposite the discontinuity 403 may cause the opposing ends 409-411 of the discontinuity 403 to close around an object that has been inserted into its opening 405. In the embodiment described above, this would allow the surface area between the c-ring 401 and the rod 205 to be substantially maximized.

In one embodiment, the notch 407 may be configured and dimensioned such that pressure at one or more points on the surface of the c-ring 401 may be more likely to cause deformation in the area substantially around the notch 407. Preferably, however, the notch 407 is not large enough to compromise the structural integrity of the c-ring 401 in the area substantially around the notch 407. Preferably, the width of the notch 407 may be about 1.5 mm or less. More preferably, the width of the notch 407 may be about 1.0 mm or less, and most preferably the width of the notch 407 may be about 0.8 mm or less. The depth of the notch 407 may also be varied as desired. Preferably, the depth of the notch 407 may be about 3 mm or less. More preferably, the depth of the notch 407 may be about 2 mm or less, and most preferably the depth of the notch 407 may be about 1 mm or less.

In one embodiment, surface of the c-ring 401 is preferably configured and dimensioned such that it may allow the connecting bodies 210-203 (FIGS. 2A-2C) to rotate along an axis that is perpendicular to a transverse axis of the rod 205. In one embodiment, this may be accomplished by using, for example, a c-ring 401 whose outer surface has a spherical curvature along its length, as shown in FIG. 4B. In one embodiment, the spherical curvature of the outer surface may be chosen according to the desired amount of axial translation that is desired for the connecting bodies 201-203. For instance, a larger spherical curvature of the outer surface of the c-ring 401 may allow the connecting bodies 201-203 to achieve greater axial translation than a smaller spherical curvature would allow.

In another embodiment, the spherical curvature of the outer surface may be chosen such that it is sufficient to prevent the c-ring 401 from disengaging with the opening 211 of the connecting body. In such an embodiment, the spherical curvature of at least a portion of the c-ring 401 may be greater than the spherical curvature of the opening of the collar 211.

Thus, it may be desirable to choose the spherical curvature of the c-ring 401 based on the corresponding spherical curvature of the opening 211, as described in more detail below. One way to describe the ability of a connecting body about the c-ring 401 by its axis of rotation. The axis of rotation is defined to be relative to the center point of the spherical surface. Preferably, the spherical curvature of the outer surface of the c-ring 401 may be chosen to allow between a 1 and 40 degree of rotation along an axis that is perpendicular to a transverse axis of the rod 205. More preferably, the spherical curvature may be chosen to allow between a 5 and 30 degrees of rotation about an axis perpendicular to a transverse axis of the rod 205, and most preferably the spherical curvature of the outer surface of the c-ring 401 may be chosen to allow between about a 15 and 25 degree of rotation about an axis perpendicular to a transverse axis of the rod 205.

In some embodiments, the surfaces of the c-ring 401 may be textured, or roughened, in order to increase the friction between the c-ring 401 and the inside of the clamp. Preferably, both the inner and outer surfaces of the c-ring 401 are textured. One advantage of texturing the surfaces of the c-ring 401 is that it is less likely to be dislodged or dislocated from its position inside the clamp. In one embodiment, the surfaces of the c-ring 401 may be manufactured with texturing, or alternately, the texturing may be added after the c-ring 401 is manufactured. Any method or apparatus may be used to add the texturing, such as beed blasting and the like.

The rod 205 may engage with the opening of the collar 211 in other manners. For example, in another embodiment the rod 205 may be inserted into a bushing. Preferably, the shape of the bushing allows the rod 205 to be slidingly engaged with the opening of the collar 211. In one embodiment, the rod 205 engages with a bushing that comprises a tapered end. Preferably, the tapered end is capable of being inserted into the opening of the collar 211. The outer surface of the bushing may have a spherical curvature, as described above with respect to the c-ring 401. One advantage of having the outer surface of the bushing include a spherical curvature is that the rod 205 may be capable of rotating and translating when it is engaged with the opening of the collar 211.

As mentioned above, one end of the bushing is preferably tapered. The angle with which the bushing is tapered may be varied as desired. Preferably, the angle is between about 0 and about 60 degrees. More preferably, the angle is between about 10 and about 30 degrees. Most preferably, the angle is between about 15 and about 25 degrees.

As mentioned above, the present invention comprises at least two connecting bodies 201-203, each of which may be capable of remaining engaged with one rod 103-105. In a preferred embodiment, each of the two connecting bodies may be substantially similar. Preferably, they are mirror images of each other. To simplify the description, only one connecting body is discussed below. However, it will be understood that the features and advantages described below applies to both connecting bodies 201-203.

Figure 5:
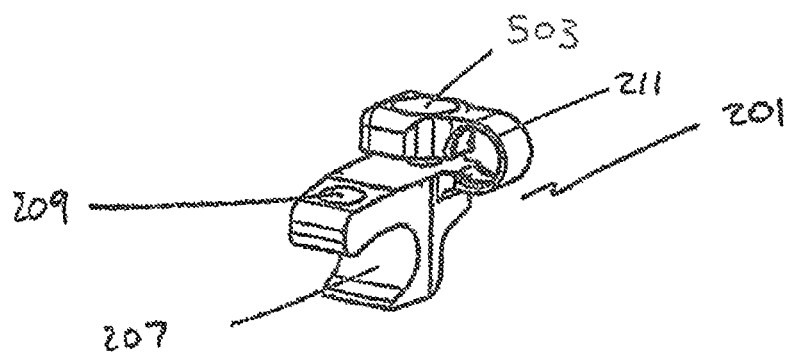
FIG. 5 is a diagram showing one embodiment of an exemplary connecting body.

FIG. 5 is a diagram showing one embodiment of connecting body 201. The connecting body comprises a receptacle 207 that is configured and dimensioned to engage with rods 103-105 (FIG. 1) from the inside. Preferably, a set screw 209 may be included to prevent the connecting body 201 from disengaging from the rods 103-105. In one embodiment, each connecting body 201-203 also comprises a collar 211 for passing the c-ring 401 and rod 205. The collar 211 may be capable of being flexed such that the c-ring 401 and the rod 205 may be positioned within the opening of the collar 211.

Once the c-ring 401 and rod 205 are inserted into the collar 211, it may be tightened around the c-ring 401 by using, for example, a screw 213.

With respect to FIG. 5, the receptacle 207 is described. As shown in FIG. 5, receptacle 207 may be selectively configured to engage rod 103-105 from the inside. In other words the receptacle 207 faces away from the area located in between rods 103-105, shown in FIG. 1. Preferably, the receptacle has a curvature that is capable of engaging with the rod 105. The curvature of the receptacle 207 may be uniform, or non-uniform. Preferably, the curvature allows the receptacle 207 to engage with the rod 103 without fixing the rod in place. One advantage of allowing the rod 103 to move slightly is that the present invention may be allowed to move slightly relative to the rod 103, preventing the vertebrae from being subjected to extra stress forces that could compromise their structural integrity.

In some embodiments, it may be desirable to substantially minimize the surface area of the receptacle 207 in order to minimize its profile. One advantage of minimizing the profile of the receptacle 207 is that it will be less likely to protrude under the skin. However, the surface area of the receptacle 207 is preferably chosen to be sufficient to engage the rod 103. Accordingly, it may be desirable to configure the bottom portion 501 such that it only engages with a portion of the rod 103. In one embodiment, the bottom portion 501 of the receptacle 207 engages with about 75% or less of the diameter of the rod 103. More preferably, the bottom portion engages with about 65% or less, and most preferably the bottom portion engages with between about 45 and 55% of the diameter of the rod 103.

The connecting body 201 preferably includes an opening 503 through which a set screw 209 may pass. In one embodiment, the opening may include threads to assist in the insertion of the set screw 209. The positioning of the opening on connecting body 201 may be chosen based on any desired factor, such as the size of the rod 103, and the like. In one embodiment, the opening may be configured and dimensioned such that it causes the set screw 209 to be inserted vertically downwards. In another embodiment, the opening may be positioned at an angle with respect to a horizontal axis, such that it causes the set screw 209 to be inserted slightly towards the receptacle. Preferably, the angle is chosen such that it allows the set screw 209 to increase the amount of force that is exerted on the rod 103. Preferably, the opening 503 allows the set screw to be inserted at an angle of between about 0 and 10 degrees relative to a horizontal axis. More preferably, the opening allows the set screw to be inserted at an angle of between about 0 and 7 degrees, and most preferably the opening allows the set screw to be inserted at an angle of between about 1 and 5 degrees relative to a horizontal axis.

In one embodiment, as the set screw 209 passes through the opening 503, it applies an off-axis, or tangential force to the rod 103. The tangential force preferably forces the rod 103 into the receptacle 207, and prevents disengagement. The shape of the shaft of the set screw may be chosen such that it aids in applying the off-axis, or tangential force to the rod 103. At least a portion of the shaft of the screw, as shown in FIG. 6B, may comprise a conical shape. One advantage of the angle of the conical shape is that it allows the set screw in applying the tangential force. Additionally, the bottom portion of the conical screw may be flattened, as shown in FIG. 6B. The flattened portion of the shaft provides the advantage of causing an edge to be formed between the flattened portion and the conical portion, thus preventing the rod 103 from disengaging from the receptacle 207. In one embodiment, the angle of a conical portion of the shaft may be chosen such that it is capable of applying a tangential force sufficient to maintain the engagement of the rod 103 and the receptacle 207. Preferably, the angle of the conical portion of the shaft of the set screw may be between about 20 and about 50 degrees. More preferably, the angle of the conical portion of the shaft may be between about 30 and about 45 degrees, and most preferably the angle of the conical portion of the shaft may be between about 25 and 40 degrees.

Figure 6A:
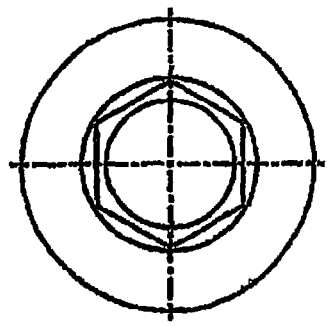
FIGS. 6A-6B are diagrams showing one embodiment of an exemplary set screw.
Figure 6B:
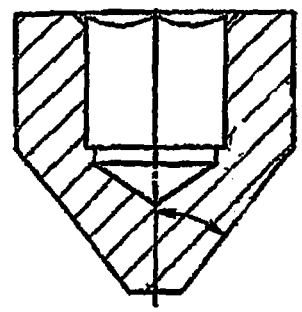

In one embodiment, shown in FIG. 6A, the head of the set screw 209 may be rounded. In order to assist with forcing the screw into opening 503, the screw may include a cavity that is capable of accommodating a tool that provides the torque necessary to force the screw into the opening 503. One advantage of including a cavity in the head of the screw is that the profile of the screw may be substantially minimized while allowing a receptacle that allows a tool to aid with the insertion of the set screw. In one embodiment, the cavity may comprise a hexagonal cavity, as shown in FIG. 6A. However, in other embodiments the cavity may comprise any shape, including, but not limited to a pentagon, triangle, and the like. In other embodiments, the head of the screw 209 may comprise a protrusion, rather than a cavity.

Figure 7:
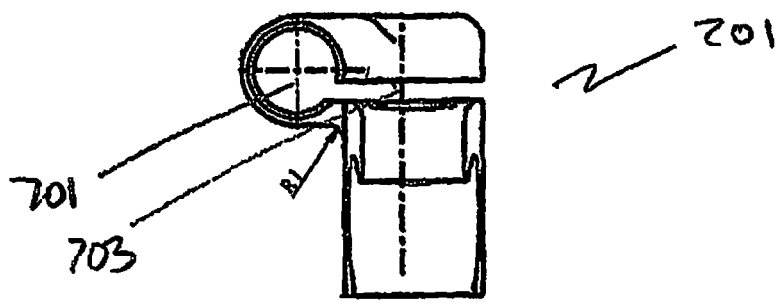
FIG. 7 is a diagram showing another view of the connecting body shown in FIG. 5.

As described above, the connecting body 201 comprises a collar 211 that is capable of engaging with the c-ring 401. As shown in FIG. 7, the collar 211 may comprise an opening 701 that may be engageable with the c-ring 401, and a portion 703 that is capable of being fastened to the connecting body 201. In this embodiment, the collar 211 may be flexed such that the opening 701 may be widened, or increased to allow the c-ring 401 to be positioned within it. After the c-ring 401 is positioned inside the opening 701 of the collar 211, the collar 211 may be tightened around the c-ring 401 using, for example, a screw 213. The screw 213 preferably passes through the portion 703 of the collar 211 and the connecting body 201 to fasten them together.

When the collar 211 is in its fastened state, opening 701 of the collar 211 is preferably engaged with the c-ring 401. In one embodiment, the opening 701 of the collar 211 may also be textured, as described above with respect to the c-ring 401. At this point, the connecting body 201 is preferably fixed in place with respect to the rod 205 and the c-ring 401. However, before the collar 211 is in its fastened state, the size of the opening of the collar 211 may be sufficient to allow for the movement of the c-ring 401 while preventing the c-ring 401 from disengaging. In one embodiment, this may be accomplished by including a spherical curvature on the inner surface of the opening 701 of the collar 211. At least a portion of the spherical curvature of the inner surface of the opening 701 of the collar 211 may be substantially smaller than the spherical curvature of the c-ring 401. In one embodiment, the spherical curvature of the inner surface of the opening 701 may be about 5% or less smaller than the spherical curvature of the c-ring 401. More preferably, the spherical curvature of the opening 701 may be about 2.5% or less smaller and most preferably the spherical curvature of the opening 701 may be about 2% or less smaller than the spherical curvature of the c-ring 401. In one embodiment, the length of the opening 701 may be varied as desired. For example, in one embodiment, the length of the opening may be substantially similar to the length of the c-ring 401. In another embodiment, the length of the opening 701 may be substantially smaller than the length of the length of the c-ring 401. Preferably, the length of the opening 701 may be about 10% or less smaller than the length of the c-ring 401. More preferably, the length of the opening

701 may be about 5% or less smaller and most preferably the length of the opening 701 may be about 2.5% smaller than the length of the c-ring 401.

Figure 8A:
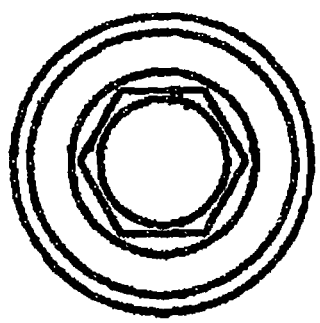
FIGS. 8A-8B are diagrams showing one embodiment of an exemplary screw.
Figure 8B:
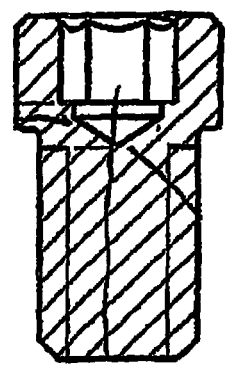

In one embodiment, the screw 213 used to fasten portion 703 of the collar to the connecting body 201 may have a substantially rounded head, as shown in FIG. 8A. The dimensions of the head may be varied as desired. However, it may be preferable to substantially minimize the dimensions of the head to minimize the profile of the present invention. The screw 213 may also include a cavity, for example, a hexagonal cavity, as described with respect to FIG. 6A. In contrast to the set screw 209, screw 213 preferably has an elongate shaft. It may be desirable to include threads on the surface of the shaft to aid in its insertion into the connecting body 201. One advantage of the elongate shaft is that the surface area of the shaft is larger compared to a conical shaft, which allows the elongate shaft to provide greater purchase into the connecting body 201. The dimensions, including the length and radius of the screw 213 may be varied as desired. In one embodiment, the length of the shaft may be chosen such that it is capable of passing through the collar and into the connecting body 201. Preferably, the length of the shaft of screw 213 may be between about 1 and 8 cm. More preferably, the length of the shaft of the screw 213 may be between about 2 and 6 cm, and most preferably the length of the shaft of the screw 213 may be between about 3 and 5 cm.

In another embodiment, the collar and the connecting body 201 may be once piece. In other words, the collar may not be capable of being flexed or opened in this embodiment. In such an embodiment, the collar may comprise a receptacle that is capable of receiving a bushing through which the rod 205 passes, as described previously. The receptacle is preferably configured and dimensioned to be complementary to the shape of the bushing. It is desirable that the bushing may be inserted into the receptacle in the collar and then forced together. The bushing and the receptacle may be forced together by using a device that is capable of exerting both transverse and downwards pressure.

As shown in FIG. 2B, the portion of the connecting body 201 that faces away from the rod 103 is tapered towards the bottom. One advantage of a tapered inner face 215 of the connecting body 201 is that clearance may be provided for the connecting body of vertebrae. In one embodiment, it is desirable to taper the inner face 215 of the connecting body in order to provide a large amount of clearance. However, the inner face 215 should be sufficient to provide structural integrity and to allow screw 213 to pass sufficiently deep into the connecting body to allow the collar 211 to be fastened.

Although the present invention has been described with reference to particular embodiments, it will be understood to those skilled in the art that the invention is capable of a variety of alternative embodiments within the spirit of the appended claims.

What is claimed is:

1. A method for stabilizing spinal elements comprising:
   providing a transverse fixation device, the transverse fixation device comprising:
   a first, second and third elongate rod;
   a connecting body comprising a receptacle facing outwards towards the first rod and away from the second rod, the connecting body further comprising a clamp;
   wherein the clamp is disposed around the third rod,
   wherein the clamp allows the connecting body to slidingly engage with e third rod,
   a screw for connecting the connecting body to the clamp, wherein the screw includes a shaft that is capable of passing through the clamp and into the connecting body; and
   wherein the third rod is laterally offset from the receptacle of the connecting body for accommodating anatomical structural elements,
   wherein the clamp, the connecting body and the receptacle are configured as a single monolithic structure
   wherein the receptacle is configured with a uniform curvature to engage between 45% and 75% of a diameter of the first rod, and
   securing the transverse fixation device to the spinal elements.

2. The method of claim 1, further comprising a c-ring disposed within the clamp.

3. The method of claim 2, wherein the c-ring comprises a notch opposing an opening.

4. The method of claim 2, wherein the c-ring comprises an outer surface having a spherical curvature and first and second five ends facing each other to define an opening.

5. The method of claim 1, wherein the clamp is u-shaped.

6. The method of claim 1, wherein the connecting body is capable of rotating about a transverse axis.

7. The method of claim 6, wherein the rotation is between about 10 and 15 degrees relative to the center of a spherical surface.

8. The method of claim 1, wherein the clamp comprises a bushing.

9. A method for stabilizing spinal elements comprising:
   providing a transverse fixation device, the transverse fixation_ device comprising:
   a first, second, and third elongate rod;
   a c-ring having first and second free ends facing each other to define an opening;
   a connecting body comprising a receptacle facing outwards towards the first rod and away from the second rod, the connecting body further comprising a clamp;
   a screw for connecting the connecting body to the clamp, wherein the screw includes a shaft that is capable of passing through the clamp and into the connecting body,
   wherein the clamp is disposed around the c-ring and the third rod, the clamp having a curved surface corresponding to the outer surface of the c-ring, and
   wherein the third rod is laterally offset from the receptacle of the connecting body for accommodating anatomical structures,
   wherein the clamp, the connecting body and the receptacle is configured as a single monolithic structure,
   wherein the receptacle is configured with a uniform curvature to engage between 45% and 75% of a diameter of the first rod, and
   securing the transverse fixation device to the spinal elements.

10. The method of claim 9, further comprising a fastener received by the clamp, wherein the fastener causes the clamp to be clamped around the third rod, thereby locking the third rod relative to the connecting body.

11. The method of claim 9, wherein the c-ring comprises a substantially cylindrical inner surface.

12. The method of claim 9, wherein the clamp is u-shaped.

13. The method of claim 9, wherein the connecting body is capable of rotating about a transverse axis.

14. The method of claim 9, wherein the clamp comprises a bushing.

15. A method of stabilizing spinal elements comprising:
providing a transverse fixation device, the transverse fixation device comprising:
- a first, second and third elongate rod;
- a first and a second one-piece connecting body, the first and second connecting bodies each comprising a receptacle facing outwards towards either the first rod or second rod and away from the other of the first rod or second rod, wherein the first connecting body comprises a first clamp disposed around one end of the third elongate rod and the second connecting body comprises a second clamp disposed around an opposite end of the third elongate rod;
- a first set screw capable of securing the first clamp to the third rod; and
- a second set screw capable of securing the second clamp to the third rod, and;
- wherein rotation of the first set screw causes the first clamp to be clamped around the third rod relative to the first connecting body, and
- wherein rotation of the second set screw causes the second clamp to be clamped around the third rod relative to the second connecting body
- wherein the third rod is laterally offset from the receptacles of the first and second connecting bodies for accommodating anatomical structural elements
- wherein the receptacle is configured with a uniform curvature to engage between 45% and 75% of a diameter of the first rod, and securing the transverse fixation device to the spinal elements.

16. The method of claim 15, further comprising a first and a second c-ring, wherein the first c-ring is disposed within the first clamp and the second c-ring is disposed within the second clamp.

17. The method of claim 16, wherein the first c-ring comprises a. notch selectively positioned on an inner face of the first c-ring and substantially opposite an opening.

18. The method of claim 15, wherein the first connecting body is capable of rotating about a transverse axis.

19. The method of claim 18, wherein the degree of rotation is about 90 degrees or less.

20. The method of claim 18, wherein the degree of rotation is about 180 degrees or less.

* * * * *